(12) United States Patent
Heinrich

(10) Patent No.: US 8,292,855 B2
(45) Date of Patent: Oct. 23, 2012

(54) ACCESS ASSEMBLY WITH ADJUSTABLE SEAL MEMBER

(75) Inventor: Russell Heinrich, Madison, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/179,612

(22) Filed: Jul. 11, 2011

(65) Prior Publication Data
US 2011/0270041 A1 Nov. 3, 2011

Related U.S. Application Data

(63) Continuation of application No. 12/276,702, filed on Nov. 24, 2008, now Pat. No. 7,988,672.

(60) Provisional application No. 61/019,908, filed on Jan. 9, 2008.

(51) Int. Cl.
*A61M 5/178* (2006.01)
(52) U.S. Cl. .......... 604/167.06; 604/167.02; 604/167.03
(58) Field of Classification Search ............. 604/167.01, 604/167.02, 167.03
See application file for complete search history.

(56) References Cited

U.S. PATENT DOCUMENTS

| | | |
|---|---|---|
| 5,209,737 A | 5/1993 | Ritchart et al. |
| 5,458,640 A | 10/1995 | Gerrone |
| 6,945,983 B2 * | 9/2005 | Dittrich et al. ................ 606/185 |
| 7,988,672 B2 * | 8/2011 | Heinrich .................. 604/167.06 |
| 2007/0118021 A1 | 5/2007 | Pokorney |

FOREIGN PATENT DOCUMENTS

| | | |
|---|---|---|
| DE | 4312147 | 1/1996 |
| WO | WO2006/020267 | 2/2006 |

OTHER PUBLICATIONS

European Search Report for corresponding EP08254057 date of mailing is Mar. 11, 2009 (3 pages).

* cited by examiner

*Primary Examiner* — Laura Bouchelle

(57) ABSTRACT

A surgical access assembly for receiving instruments of various diameters is disclosed. The access assembly includes a housing defining a longitudinal axis and having a longitudinal opening for passage of a surgical instrument. The access assembly may also include a mechanism disposed within the housing and having a passageway for reception and passage of the surgical instrument in substantial sealed relation therewith. The mechanism may be adapted for reciprocal longitudinal movement within the housing between a first position corresponding to a first dimension of the passageway and a second position corresponding to a second dimension of the passageway.

The mechanism may include a single seal element or first and second seal elements. The seal elements may be adapted for lateral movement during longitudinal movement of the seal. The first and second seal elements may be in at least partial overlapping relation when in the first position of the seal. The access assembly may include a lock or latch for preventing movement of the seal elements.

28 Claims, 9 Drawing Sheets

ACCESS ASSEMBLY WITH ADJUSTABLE SEAL MEMBER

CROSS REFERENCE TO RELATED APPLICATIONS

This application is a Continuation of U.S. application Ser. No. 12/276,702, filed Nov. 24, 2008 now U.S. Pat. No. 7,988,672, which claims the benefit of and priority to U.S. Provisional Application Ser. No. 61/019,908, filed on Jan. 9, 2008, entitled "ACCESS ASSEMBLY WITH ADJUSTABLE SEAL MEMBER", the entire contents of which are hereby incorporated herein by reference.

BACKGROUND

1. Technical Field

The present disclosure relates generally to systems for accessing the body, and more particularly, to trocar systems configured for sealably receiving endoscopic instruments of various diameters.

2. Background of Related Art

Trocars and other access assemblies are used by surgeons to operate on a patient without having to create large incisions that may become infected and may cause major scaring. Access assemblies are known in the art, as are the instruments inserted therethrough for operating within the body cavity. Typically an access assembly comprises two major components, a sleeve including a housing and a cannula, and an obturator.

Accessing the body cavity using an access assembly is a multi-step process. An incision is initially made in the skin using a scalpel or other cutting instrument. Some access assemblies may include a cutting blade or sharpened distal end for performing this function. The obturator, having been inserted into the sleeve of the cannula, is directed through the incision in the skin. By applying pressure against the proximal end of the obturator, the sharpened point of the obturator is forced through the skin until it enters the body cavity. The cannula is inserted through the perforation made by the obturator and the obturator is withdrawn, leaving the trocar cannula as an access way to the body cavity.

In order to provide a greater space in which a surgeon may operate and to increase visibility of the tissue being operated on, the body cavity is generally insufflated. To avoid gas leakage from within the cavity prior to or during insertion of an instrument through the cannula, and as instruments are being removed and replace, various seal members have been developed. Conventional access systems generally include one or more seals configured for use with endoscopic instruments of the same or similar diameters. In this manner, all of the instruments inserted through the access assembly must be of substantially similar diameter, otherwise a proper seal will not form between the instrument and the housing. An improper seal may result in leakage of the insufflation gas.

However, not all endoscopic instruments have similar diameters. An instrument for performing one procedure may have a different diameter from a second instrument for performing the same procedure, just as instruments for performing various procedures may have different diameters from one another. Successful completion of a procedure may require the use of various instruments throughout the procedure. Thus, completing a procedure using multiple endoscopic instruments may require the use of more than one access assembly each of a different size.

Therefore, it would be beneficial to have an access assembly that is configured to receive endoscopic instruments of differing diameters.

SUMMARY

According to an aspect of the present disclosure, a surgical access assembly is provided. The surgical access assembly includes a housing defining a longitudinal axis and having a longitudinal opening for passage of a surgical instrument, and defining proximal and distal ends. The access assembly further includes a seal disposed within the housing and having a passageway for reception and passage of the surgical instrument in substantial sealed relation therewith. The seal may be adapted for reciprocal longitudinal movement within the housing between a first position corresponding to a first dimension of the passageway and a second position corresponding to a second dimension of the passageway.

The first position of the seal may correspond to a proximal position while the second position of the seal corresponds to a distal position. The first dimension of the passageway may be less than the second dimension of the passageway.

The seal may include a single seal element or first and second seal elements. The seal elements may be adapted for lateral movement during longitudinal movement of the seal. The seal elements may further be adapted for lateral movement during longitudinal movement of the seal between the first and second positions thereof. The first and second seal elements may be adapted to move laterally outwardly upon movement of the seal from the first position to the second position. The first and second seal elements may be in at least partial overlapping relation when in the first position of the seal. A base may be mounted to each seal element.

The surgical access assembly may include a latch for preventing the movement of the first base member. The latch is pivotally mounted across the passageway and is configured to engage the first base member, thereby preventing movement thereof. The latch may include a notch, groove, tab, cam or hook configured to engage the first base member. Rotation of the latch causes disengagement thereof with the first base member, thereby permitting movement of the first and second base members.

In an alternate embodiment, the surgical access assembly may further include a lock mounted to the housing for selectively securing the seal at the first position or the second position thereof. The lock may include a lever intersecting the longitudinal opening of the housing and operatively connected to the seal. The lever may be positioned to engage the surgical instrument during passage through the housing to thereby facilitate movement of the seal from the first position to the second position thereof.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

DESCRIPTION OF PREFERRED EMBODIMENTS

Figure 1:
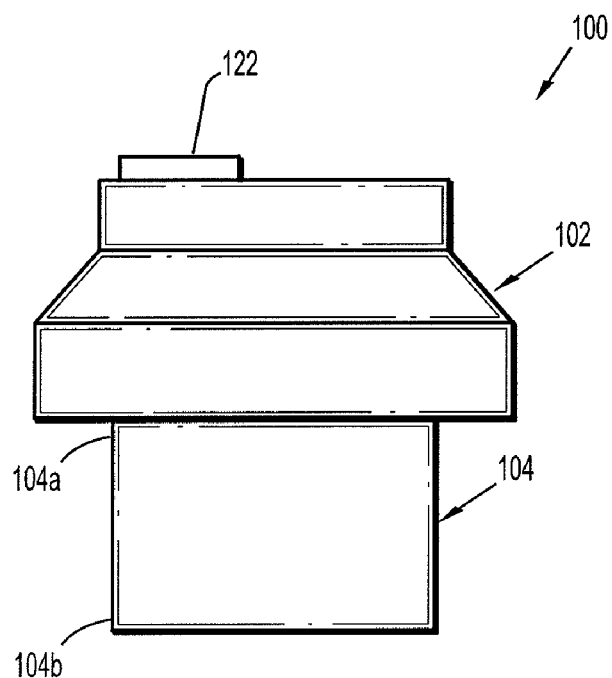
FIG. 1 is a side perspective view of a trocar assembly according an embodiment of the present disclosure.

Referring now to the drawings wherein like reference numerals illustrate similar components throughout the several views. As shown in the drawings and as described throughout the following description, as is traditional when referring to relative positioning on an object, the term "proximal" refers to the end of the apparatus which is closer to the user and the term "distal" refers to the end of the apparatus which is further from the user.

Figure 2:
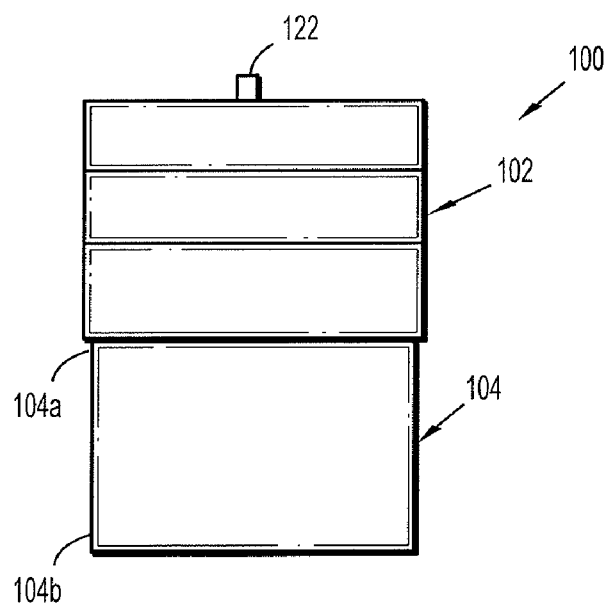
FIG. 2 is a front perspective view of the trocar assembly of FIG. 1.

FIGS. 1-8 illustrate an access assembly 100 in accordance with the principles of the present disclosure. Referring initially to FIGS. 1 and 2, access assembly 100 includes a housing 102 and a cannula 104 extending distally therefrom. Access assembly 100 may be configured for use with any known endoscopic or laparoscopic instrument. Cannula 104 is configured to be inserted through the skin into a body cavity with the aid of an obturator (not shown). Cannula 104 may instead include a blade or piercing tip for penetrating through the skin and into a body cavity. Cannula 104 may be integral formed with housing 102. Alternatively, cannula 104 may be configured for selectable engagement with trocar housing 102.

Cannula 104 forms a substantially tubular member having proximal and distal ends 104a, 104b. Cannula 104 may be composed of plastic, metal, polymers or other suitable material. Cannula 104 may be disposable, or in the alternative, reusable. Cannula 104 may be rigid, or alternatively, cannula 104 may be flexible. Distal end 104b of cannula 104 may be open. Distal end 104b may instead be configured to include one or more seal members 104' for receiving an instrument therethrough. Cannula 104 may be of any configuration and of any length or diameter. Thus, it is appreciated that the embodiments of the present disclosure are not limited by the configuration of cannula 104 and may be configured for use with any conceivable cannula configuration.

Figure 3:
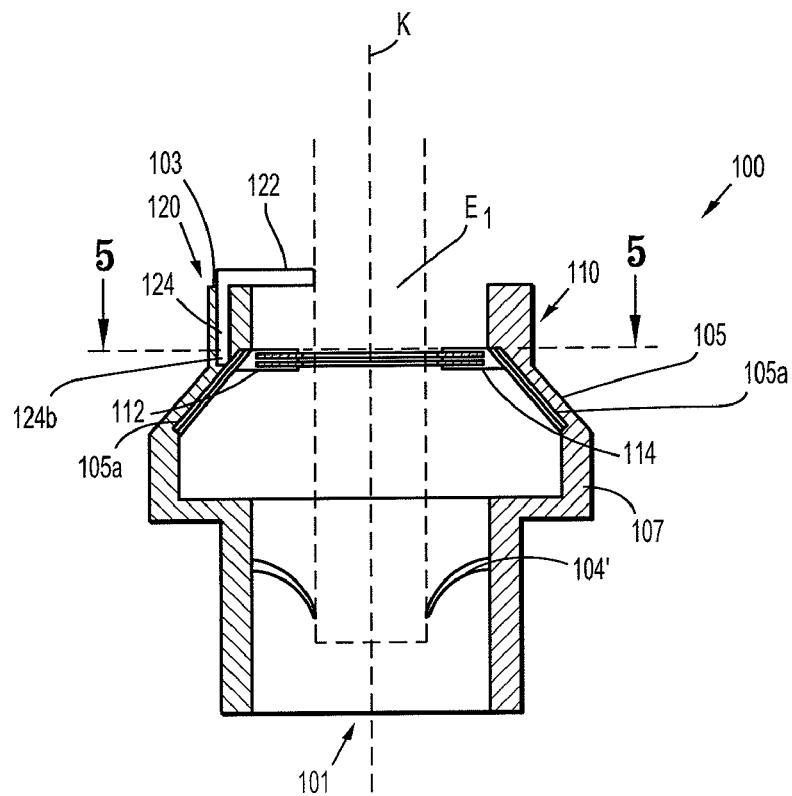
FIG. 3 is a cross-sectional side view of the trocar assembly of FIGS. 1 and 2, in a first position.
Figure 4:
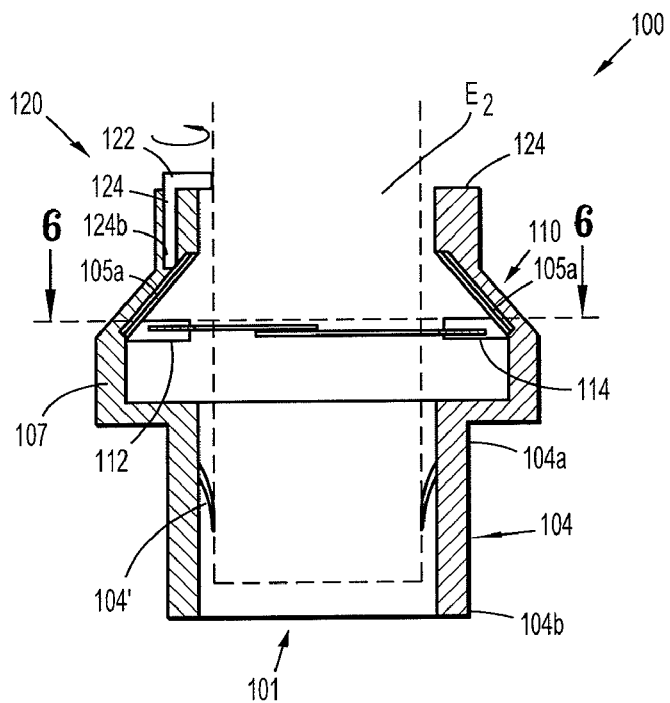
FIG. 4 is a cross-sectional side view of the trocar assembly of FIGS. 1-3, in a second position.

Referring now to FIGS. 3 and 4, housing 102 of access assembly 100 defines longitudinal axis "k" and has a longitudinal passageway 101 therethrough configured for selectively receiving endoscopic instruments of various diameters. Housing 102 may form a generally rectangular cross-sectional shape, as shown, however, alternate configurations are also envisioned, including but not limited to, circular, square and triangular. Housing 102 defines a first annular portion 103, a slanted middle portion 105, and a second annular portion 107. First annular portion 103 is of a larger diameter than second annular portion 107, and preferably includes a diameter substantially similar to the diameter of cannula 104. Slanted middle portion 105 connects first and second annular portions 103, 107. As will be discussed below, slanted middle portion 105 defines substantially T-shaped grooves 105a extending between first and second annular portions 105, 107.

Figure 11:
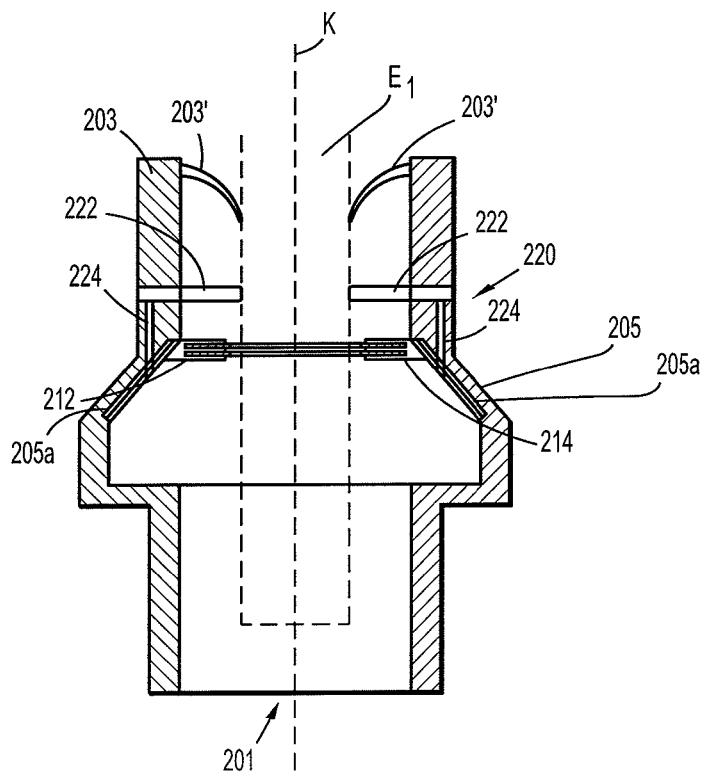
FIG. 11 is a cross-sectional side view of an alternate embodiment of a trocar assembly, in a first position.
Figure 12:
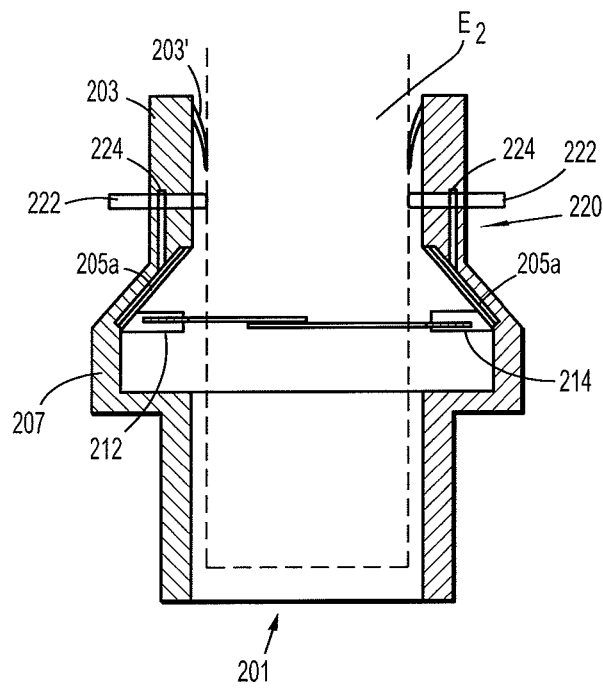
FIG. 12 is a cross-sectional side view of the trocar assembly of FIG. 11, in a second position.
Figure 13:
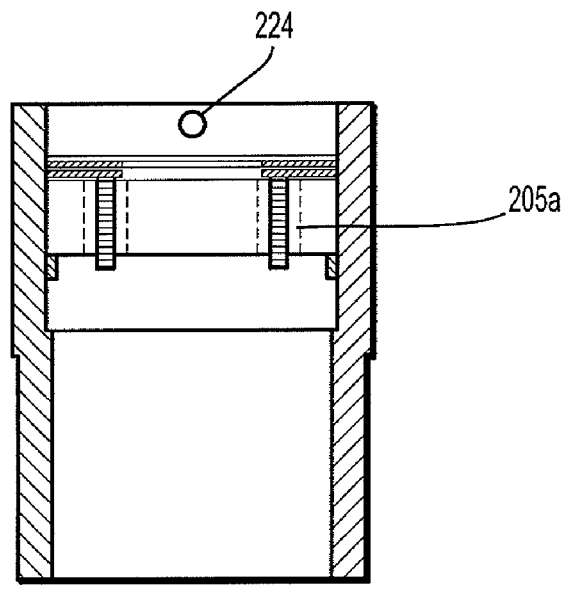
FIG. 13 is a cross-sectional top view of the trocar assembly of FIGS. 11 and 12 in the first position.
Figure 14:
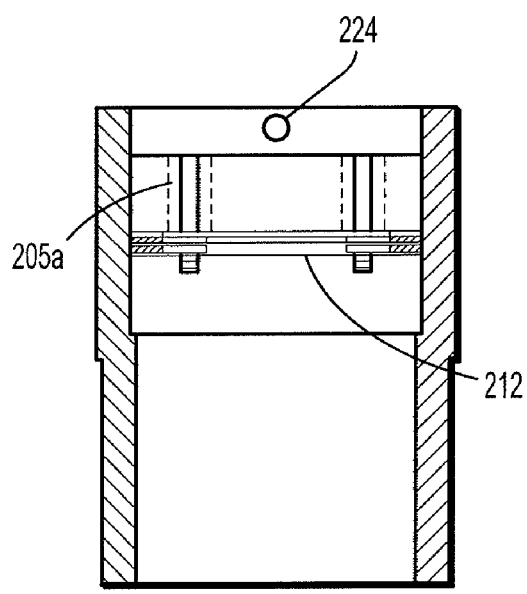
FIG. 14 is a cross-sectional top view of the trocar assembly of FIGS. 11-13, in the second position.
Figure 15:
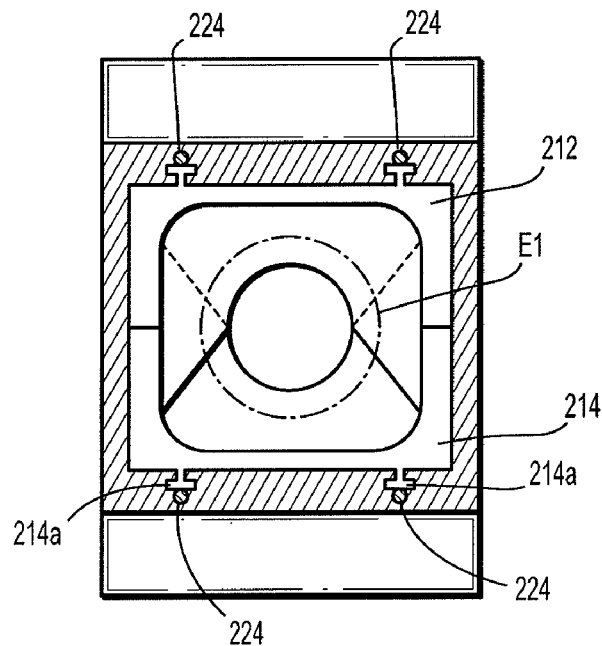
FIG. 15 is a cross-sectional side view of the trocar assembly of FIGS. 11-14, in the first position.
Figure 16:
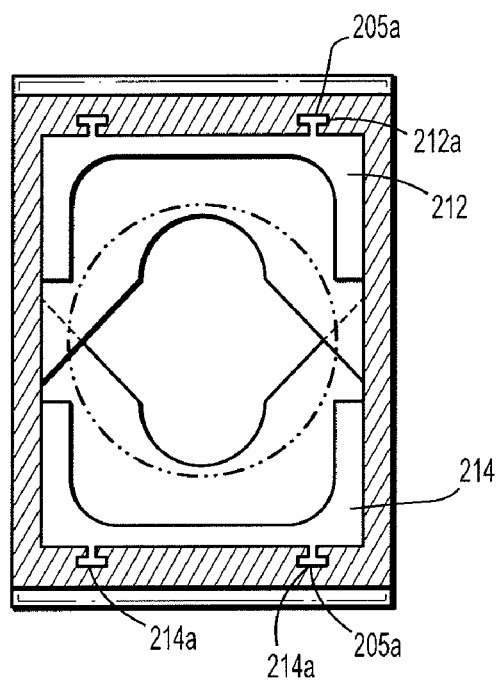
FIG. 16 is a cross-sectional side view of the trocar assembly of FIGS. 11-15, in the second position.

Still referring to FIGS. 3 and 4, housing 102, includes an adjustable seal mechanism 110. As will be described below, adjustable seal mechanism 110 is configured to receive instruments of differing diameters therethrough. Seal mechanism 110 may be configured to establish a substantial sealed relation with the instruments inserted therethrough. Alternatively, seal mechanism 110 may be configured to restrict or limit the movement of an instrument inserted therethrough. In this manner, a seal member (203', 104') positioned proximal (FIG. 11) or distal (FIG. 3) of seal mechanism 110 may maintain a seal about the instrument inserted therethrough while seal mechanism 110 may operate to prevent excess movement of the instrument which may compromise the integrity of the seal.

Seal mechanism 110 includes a first base member 112 and a second base member 114. First and second base members 112, 114 define substantially planar members configured to be received within passageway 101 of housing 102. First and second base member 112, 114 are adapted to slide in a general longitudinal direction with respect to the longitudinal axis "k" and in a lateral direction. First and second base members 112, 114 include seal members 113, 115, respectively, extending therefrom. As will be discussed below, first and second base members 112, 114 and corresponding seal members 113, 115, cooperate to receive instruments of different diameters.

Figure 9:
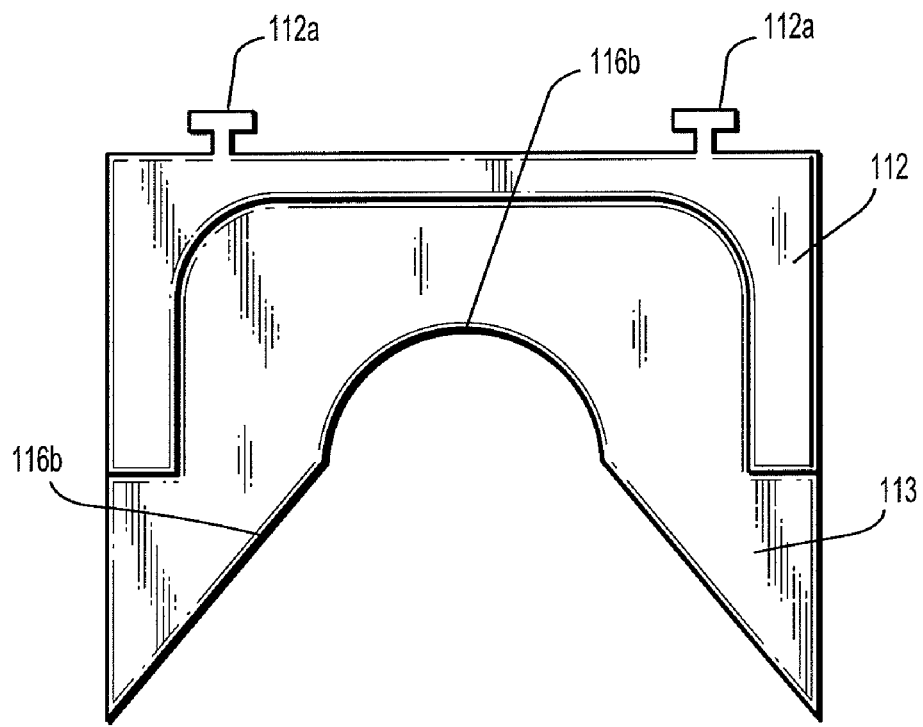
FIG. 9 is a top view of a first base member of the trocar assembly of FIGS. 1-8.
Figure 10:
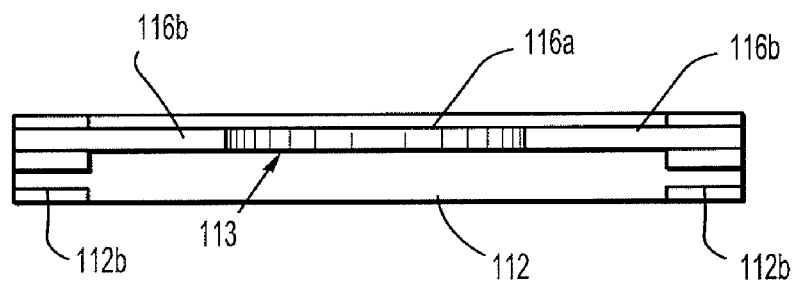
FIG. 10 is an end view of the first base member of FIG. 9

Turning now to FIGS. 9 and 10, because first and second seal members 112, 114 are substantial identical, base members 112, 114 will be described as relates to first base member 112. First base member 112 defines a substantially C-shaped member defining an opening including seal member 113 extending therefrom. First base member 112 may be constructed of plastic, metal, polymer or other like material. Seal member 113 may be constructed of rubber, plastic, polymer or other suitable material. Seal member 113 defines a semi-circular opening 116a configured to corresponding with a semi-circular opening 118a (FIG. 6) defined by seal member 115 extending from second base member 114 for receiving an endoscopic instrument E1 (FIGS. 3 and 5) having a first diameter. Seal member 113 defines an increasingly wider opening 116b extending from first base member 112. As will be described below, seal members 113, 115 of first and second base members 112, 114, respectively, are configured such that as first base member 112 moves relative to second base member 114, corresponding openings 116b, 118b formed in the respective seal members 113, 115 adjust in size to accommodate instruments of different diameters.

Still referring to FIGS. 9 and 10, first base member 112 includes a pair of outwardly extending tabs 112a. Tabs 112a are configured to be received within grooves 105a (FIGS. 3 and 4) defined in slanted portion 105 of housing 102 and may slide within groove 105a. Tabs 112a may be substantially T-shaped as shown, or may instead include any other suitable configuration. Tabs 112a are configured to permit first base member 112 to slide within grooves 105a. Preferably, tabs 112a and corresponding tabs 114a (FIGS. 5 and 6) formed on second base member 114 are configured to maintain first and second base members 112, 114 in a horizontal relationship with one another.

It is envisioned that base members 112, 114 may include any number of tabs. Although grooves 105a are shown as only being defined on two opposing sides of housing 102, it is envisioned that additional grooves may be formed on the other two opposing sides of housing 102. In this manner, corresponding tabs formed on first and/or second base members 112, 114 could be received in the grooves, thereby more securely retaining first and/or second base members 112, 114 within housing 102. In an alternate embodiment, it is envisioned that slanted portion 105 of housing 102 may instead define the elongated tabs or protrusions for being received in a corresponding groove defined by the first and second base members. In this manner, the base members would be slidingly received about the tabs formed in the housing.

Figure 5:
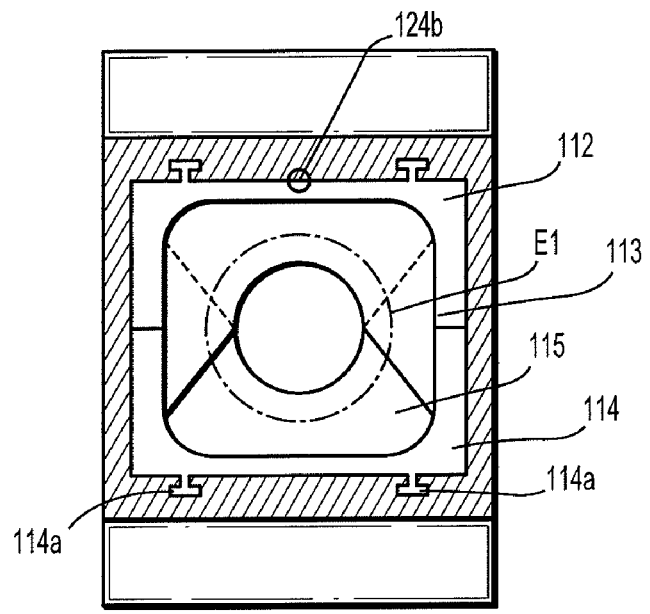
FIG. 5 is a cross-sectional top view of the trocar assembly of FIG. 3, in the first position, taken along line 5-5.
Figure 6:
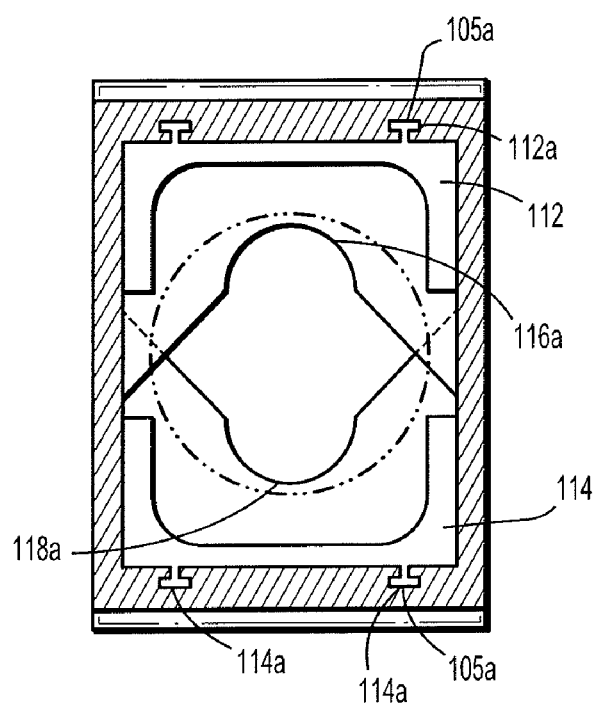
FIG. 6 is a cross-sectional top view of the trocar assembly of FIG. 4, in the second position, taken along line 6-6.
Figure 7:
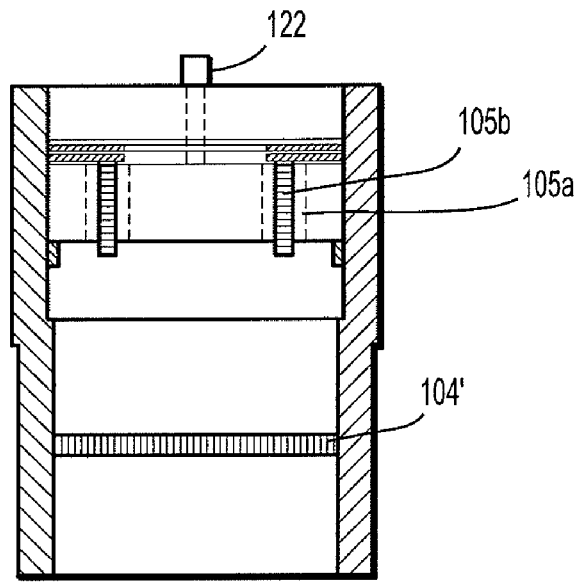
FIG. 7 is a cross-sectional side view of the trocar assembly of FIGS. 1-6, in the first position.
Figure 8:
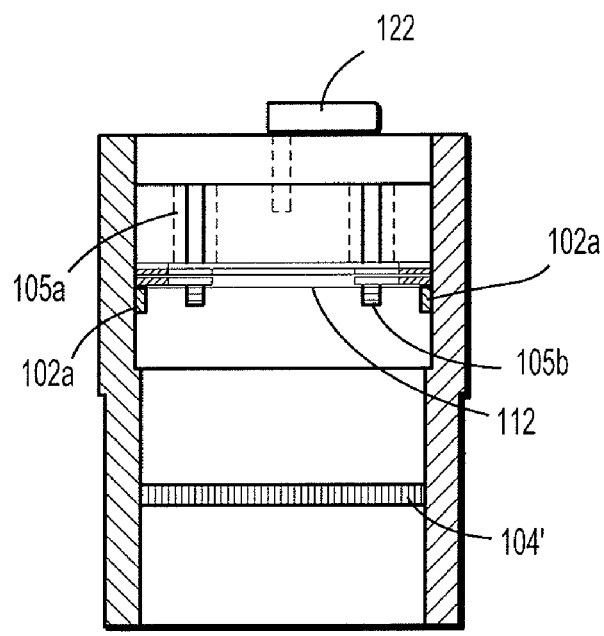
FIG. 8 is a cross-sectional side view of the trocar assembly of FIGS. 1-7, in the second position.

With particular reference now to FIG. 10, first base portion 112 defines slots 112b for receiving portions of seal member 115. Although not shown, second base member 114 includes slots for receiving corresponding portions of seal member 113 (FIGS. 5 and 6). As will be discussed below, as first and second base members 112, 114 move toward one another, seal member 115 of second base member 114 is received within slots 112b defined by first base member 112. At the same time, seal member 113 of first base member 112 is received within the slots defined by second base member 112.

It is envisioned that adjustable seal mechanism 110 may include more than two base members appropriately configured for selectively receiving instruments of differing diameters. It is further envisioned that each of the base members may include more than one seal member. By providing more than one seal member per base member the seal members may be overlapped to increase the integrity of the seal. In an alternate embodiment, it is envisioned that the seal mechanism may include single seal member. In this manner, the seal member would stretch radially during longitudinal motion thereof.

Referring back to FIGS. 3 and 4, adjustable seal mechanism 110 may further include a locking mechanism for preventing the movement of first and second base members 112, 114. One example of a locking mechanism is shown generally as latch 120. Latch 120 is a substantially L-shaped member including a base 122 and a locking arm 124. Base 122 pivotally extends into passageway 101 of housing 102. Locking arm 124 extends distally within housing 102. Distal end 124b of locking arm 124 may include a notch, groove, tab, cam or hook (not shown) for selectively engaging first base member 112 and preventing movement thereof. Distal end 124b of locking arm 124 is configured such that when locking arm 124 is rotated distal end 124b disengages first base member 112. Locking arm 124 may be rotated by pivoting base 122 of latch 120 from across passageway 101 prior to insertion of an instrument E2.

With reference now to FIGS. 3-6, in operation access assembly 100 operates to sealingly receive instruments having a range of different diameters. In a first position (FIGS. 3 and 5), adjustable seal mechanism 110 is in a locked position. First and second base members 112, 114 are received within grooves 105a defined in slanted middle portion 105 of housing 102. As shown, instrument E1 may be received within passageway 101 without encountering latch 120. In this manner, distal end 124b of locking arm 124 remains engaged with first base member 112, thereby preventing movement of first and second base members 112, 114. As discussed above, when seal mechanism 110 is in a first position, a portion of seal member 113 is received within slot 114b formed in second base member 114 and a portion of seal member 115 is received within slot 112b formed in first base member 112. Additionally, first and second base members 112, 114 may be configured to engage one another to assist in synchronized movement and/or to reduce deflection upon insertion of an instrument therethrough. For example, first and second base members 112, 114 may be operationally connected with one another by rail or other mechanical fastener suitable for permitting lateral movement of first and second base members 112, 114 relative to one another. In this first position, seal mechanism 110 operates as a conventional seal member, receiving instrument E1.

Turning now to FIGS. 4 and 6, access assembly 100 may be configured in a second position for receiving instrument E2 having a larger diameter. Prior to insertion of instrument E2 into passageway 101, base 122 of latch 120 is pivoted from within passageway 101. The pivoting of base 122 causes the rotation of locking arm 124. The rotation of locking arm 124 cause the disengagement of distal end 124b thereof from first base member 112, thereby permitting the movement of first and second base members 112, 114 relative to housing 102. As instrument E2 engages seal members 113, 115, first and second base members 112, 114 translate distally within housing 102. Distal translation of first and second base members 112, 114 causes first and second base member 112, 114 to move in an outward or lateral direction with respect to the longitudinal axis. Distal translation of first and second base members 112, 114 continues until an opening large enough to sealingly receive instrument E2 therethrough is achieved. Housing 102 may include a lip or ridge 102a (FIG. 8) to prevent excessive deflection of seal members 113, 115 when in this second position as instrument E2 is inserted therethrough. Once instrument E2 has been inserted through seal members 113, 115, seal mechanism 110 operates as a conventional seal member, sealingly receiving instrument E2.

Springs 105b may be included in grooves 105a for biasing first and second base members 112, 114 proximally within housing 102. In this manner, seal members 113, 115 are forced closer together, thereby decreasing the opening formed therebetween and increasing the integrity of the seal formed about instrument E2. Springs 105b also cause the return of first and second base members 112, 114 to a first position upon removal of instrument E2 from within housing 102. In this manner, access assembly 100 may be reused.

In an alternate embodiment, adjustable seal mechanism 110 may be configured to include predetermined stops or recess formed in housing 102 for forming a seal opening of predetermined sizes. In another embodiment, seal mechanism 110 may be externally adjustable using tabs extending through housing 102. By pushing distally on the tabs extending through housing 102, a surgeon may be able to set the seal opening prior to insertion of an instrument into housing 102. Adjustable seal mechanism 110 may also include visual indicators to indicate the degree of opening of seal members 113, 115. The visual indicators may extend through the housing, or the housing may instead include a clear portion for viewing the position of first and/or second base member 112, 114. Housing 102 may include markings corresponding to the size of the opening formed therein. In yet another embodiment, locking mechanism 120 may be configured to permit selective movement of first and second base members 112, 114 within housing 102.

Referring now to FIGS. 11-16, shown is an alternate embodiment of the present disclosure shown generally as adjustable seal mechanism 210. Adjustable seal mechanism 210 is substantially similar to seal mechanism 110 and will only be discussed as relates to the differences therebetween. Adjustable seal mechanism 210 includes a locking mechanism 220 for preventing the movement of first and second base members 212, 214. Locking mechanism 120 is maintained with first annular portion 203 of housing 202 and extends within slanted middle portion 205. Locking mechanism 220 includes a pair of levers 222 extending into passageway 201. Each of levers 222 are retractably maintained within passageway 201 by a spring or other biasing means (not shown). Levers 222 engage corresponding locking pins 224. Locking pins 224 are biased proximally within housing 202. Levers 222 include a notched or cammed surface (not shown) which engage locking pins 224 when levers 222 are in an extended condition, causing locking pins 224 to extend into groove 205a. Extension of locking pins 224 into grove 205a prevents movement of first and second base members 212, 214.

Insertion of an instrument into housing 202 large enough to engage levers 222 causes the retraction of levers 222 within housing 202. Levers 222 are configured such that the retraction thereof causes the retraction of locking pins 224 from within grooves 205a, thereby permitting the movement of first and second base members 212, 214. Locking mechanism 220 may be configured such that return of levers 222 to the initial, extended position causes the extension of locking pins 224 back into grooves 205a. In this manner, first and second base members 212, 214 may then again be locked into position within housing 202.

Seal mechanism 210 may further include a seal member 203' positioned within first annular portion 203 of housing 202. Seal member 203' may be configured to receive an instrument E1 (FIG. 11), E2 (FIG. 12) therethrough. Seal member 203' may operate in conjunction with seal mechanism 210 to maintain instrument E1, E2 therethrough. In this manner, seal member 203' may operate to form the seal about instrument E1, E2 while seal mechanism 210 prevents excess movement thereof that may compromise the integrity of the seal.

Figure 17:
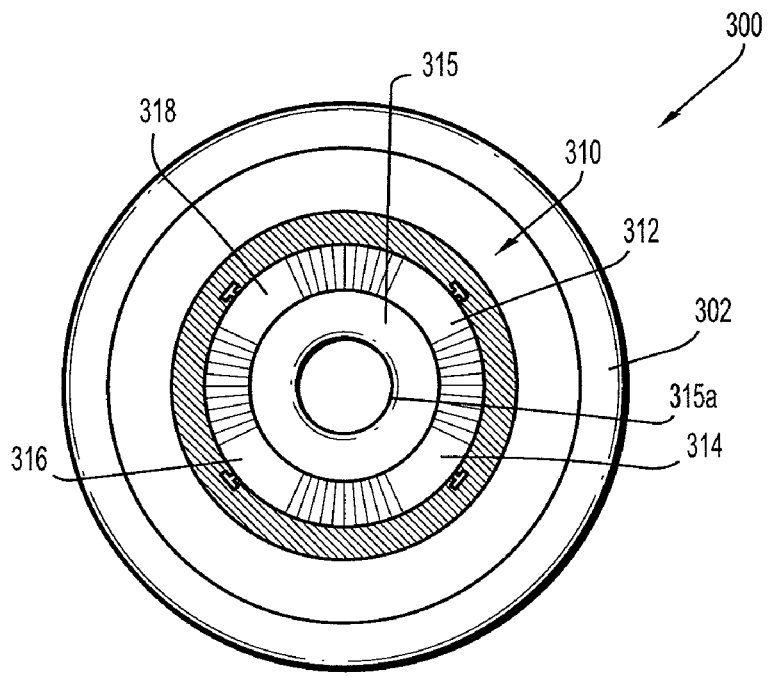
FIG. 17 is a cross-sectional top view of another embodiment of a trocar assembly, in a first position.
Figure 18:
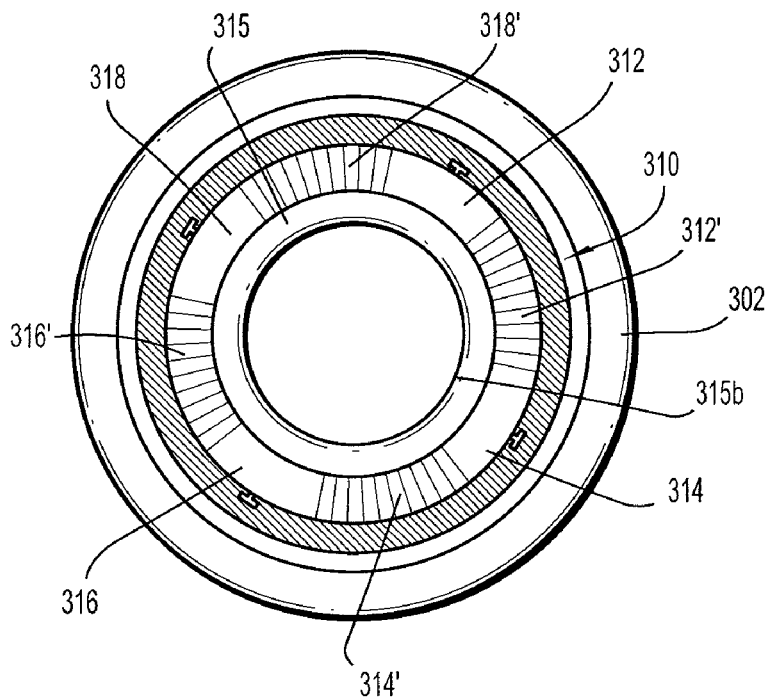
FIG. 18 is a cross-sectional top view of the trocar assembly of FIG. 17, in a second position.

Turning now to FIGS. 17 and 18, another embodiment of the present disclosure is shown generally seal mechanism 310. Seal mechanism 310 includes a plurality of base members 312, 314, 316, 318 slideably mounted within housing 302 of trocar assembly 300. Seal mechanism 310 may include any number of base members. Base members 312, 314, 316, 318 are operably connected to a seal member 315. Seal member 315 may be composed of rubber, polymer or other suitable material. As will be discussed below, when seal mechanism 310 is in a first position (FIG. 17), seal member 315 defines a first opening 315a for receiving an instrument E1 therethrough. When seal mechanism 310 is in a second position (FIG. 18), seal member 315 is stretched to form a second opening 315b for receiving an instrument E2 having a larger diameter.

Base member 312, 314, 316, 318 include spacers 312', 314', 316', 318', respectively, operably positioned therebetween. Spacers 312', 314', 316', 318' are configured to maintain a sealed connection between base members 312, 314, 316, 318 in at least a first position (FIG. 17) and a second position (FIG. 18). Spacers 312', 314', 316', 318' may define an accordion-like configuration, as shown, capable of extending as seal mechanism 310 is moved from the first position to the second position. Alternatively, spacers 312', 314', 316', 318' may define flaps, wedges or other similar structures for maintaining the seal between base members 312, 314, 316, 318 as seal mechanism 310 in at least a first and second position.

Referring initially to FIG. 17, seal mechanism 310 is shown in a first position. In this first position, seal member 315 of seal mechanism 310 defines an opening 315a sized to receive an instrument E1 (FIGS. 3 and 11) having a first diameter. Spacers 312', 314', 316', 318', operably positioned between base members 312, 314, 316, 318, respectively, are in a retracted or relaxed condition. In operation, seal mechanism 310 may be moved from the first position to the second position (FIG. 18) as described above with respect to seal mechanisms 110, 210. In a second position, seal member 315 of seal mechanism 310 is stretched or otherwise expanded to define an opening 315b sized to receive an instrument E2 (FIGS. 4 and 12) having a second, larger diameter.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims append hereto.

What is claimed is:

1. A surgical access assembly comprising:
a housing defining a longitudinal axis and having a longitudinal opening extending therethrough for passage of a surgical instrument, the housing having mounting structure associated therewith;
a sleeve extending from the housing and dimensioned for insertion through tissue; and
a seal mechanism disposed within the housing, the seal mechanism including first and second seal elements defining a passageway for reception and passage of the surgical instrument therethrough in a substantially sealed relation therewith, the first and second seal elements operatively mounted to the mounting structure of the housing and adapted to move between first and second longitudinal positions relative to the housing, whereby during longitudinal movement of the first and second seal elements from the first longitudinal position to the second longitudinal position, the mounting structure of the housing cooperates with the first and second seal elements to cause a change in a dimension of the passageway from a first dimension to a second dimension different than the first dimension.

2. The surgical access assembly of claim 1, wherein the first and second seal elements are adapted for radial outward lateral movement during longitudinal movement of the first and second seal elements from the first longitudinal position to the second longitudinal position.

3. The surgical access assembly according to claim 2, wherein the first and second seal elements are in at least partial overlapping relation when in the first position of the mechanism.

4. The surgical access assembly according to claim 2, including a base mounted to each seal element.

5. The surgical access assembly of claim 1, further including a locking mechanism mounted to the housing for selectively securing the first and second seal elements at the first longitudinal position.

6. The surgical access assembly according to claim 5, wherein the locking mechanism includes a latch for selectively securing the seal mechanism at the first position thereof.

7. The surgical access assembly according to claim 1, wherein the first longitudinal position of the first and second seal elements corresponds to a proximal position and the second position of the first and second seal elements corresponds to a distal position.

8. The surgical access assembly according to claim 7 wherein the first dimension of the passageway is less than the second dimension of the passageway.

9. The surgical access assembly according to claim 1, wherein the housing includes a tapered portion, the tapered portion having the mounting structure.

10. The surgical access assembly according to claim 9, wherein the seal mechanism is disposed within the tapered portion.

11. The surgical access assembly according to claim 1 wherein the mounting structure is longitudinally fixed within the housing.

12. The surgical access assembly according to claim 1, wherein the seal mechanism includes first and second base members connected to the first and second seal elements, respectively, the first and second base members operatively coupled to the mounting structure of the housing and adapted to cooperatively longitudinally move upon longitudinal movement of the first and second seal elements between the first and second longitudinal positions.

13. The surgical access assembly according to claim 12, wherein the mounting structure of the housing includes a tapered portion arranged at an oblique angle with respect to the longitudinal axis.

14. The surgical access assembly according to claim 13, wherein the first and second base members each include one of a tab or groove and the tapered portion of the housing includes the other of a tab or groove, the tabs received within the grooves to permit longitudinal sliding movement of the first and second base members during movement of the first and second seal elements between the first and second longitudinal positions.

15. A surgical access assembly, which comprises:
a housing defining a longitudinal axis and having a longitudinal opening extending therethrough for passage of a surgical instrument; and
a seal mechanism disposed within the housing and having a passageway for reception and passage of the surgical instrument therethrough in a substantially sealed relation therewith, the seal mechanism adapted for reciprocal longitudinal and lateral movement within the housing between at least a first position corresponding to a first dimension of the passageway and a second position corresponding to a second dimension of the passageway, the seal mechanism including:
a substantially annular seal;
a plurality of base members operatively connected to the annular seal; and
a spacer between adjacent base members.

16. The surgical access assembly according to claim 15, wherein the annular seal is configured to stretch upon movement of the seal mechanism from the first position to the second position.

17. A surgical access assembly, which comprises:
a housing defining a longitudinal axis and having a longitudinal opening extending therethrough for passage of a surgical instrument;
a seal mechanism disposed the housing and having a passageway for reception and passage of the surgical instrument therethrough in a substantially sealed relation therewith, the seal mechanism adapted for reciprocal longitudinal and lateral movement within the housing between at least a first position corresponding to a first dimension of the passageway and a second position corresponding to a second dimension of the passageway; and
a lever intersecting the longitudinal opening of the housing and operatively connected to the seal mechanism, the lever positioned to engage the surgical instrument during passage through the housing to thereby facilitate movement of the seal mechanism from the first position to the second position thereof.

18. A surgical access assembly comprising:
a housing;
a sleeve extending from the housing and dimensioned for insertion through tissue, and defining a longitudinal axis, the sleeve and the housing having a longitudinal passage extending therethrough for passage of a surgical instrument; and
at least one seal disposed within the housing and having an inner seal segment adapted to engage a surgical object and an outer base segment connected to the inner seal segment, the at least one seal slidably mounted to the housing for longitudinal movement relative to the housing from a first longitudinal position to a second longitudinal position to cause a corresponding change in an inner dimension of the inner seal segment whereby upon movement of the at least one seal element toward the second longitudinal position, the outer base segment moves in a radial outward direction to increase the inner dimension of the inner seal element.

19. A surgical access assembly, which comprises:
a housing;
a sleeve extending from the housing and dimensioned for insertion through tissue, and defining a longitudinal axis, the sleeve and the housing having a longitudinal passage extending therethrough for passage of a surgical instrument; and
at least one seal disposed within the housing and having an inner seal segment adapted to engage a surgical object and an outer base segment connected to the inner seal segment, the outer base segment being coupled to the housing in sliding relation therewith such that the at least one seal is longitudinally moveable relative to the housing from a first longitudinal position to a second longitudinal position whereby upon movement of the at least one seal element toward the second longitudinal position, the outer base segment moves in a radial outward direction to increase the inner dimension of the inner seal element.

20. The surgical access assembly according to claim 19, wherein the at least one seal is normally biased toward the first longitudinal position.

21. The surgical access assembly according to claim 19, wherein the at least one seal includes an annular seal, the annular seal dimensioned and adapted to stretch upon movement from the first longitudinal position to the second longitudinal position to increase the inner dimension of the inner seal element.

22. The surgical access assembly according to claim 21, wherein the annular seal includes a plurality of outer base elements coupled to the housing.

23. The surgical access assembly according to claim 22, wherein the annular seal includes a spacer between adjacent outer base elements, the spacer dimensioned to facilitate expansion of the annular seal to increase the inner dimension of the annular seal upon movement from the first longitudinal position to the second longitudinal position.

24. The surgical access assembly according to claim 23, wherein the spacer defines one of an accordion, flap or wedge general structure.

25. A surgical access assembly, which comprises:
a housing;
a sleeve extending from the housing and dimensioned for insertion through tissue, and defining a longitudinal axis, the sleeve and the housing having a longitudinal passage extending therethrough for passage of a surgical instrument; and
first and second seals disposed within the housing, each of the first and second seals including an outer base segment and an inner seal segment adapted to engage a surgical object, the outer base segments being slidably coupled to the housing such that the first and second seals are longitudinally moveable relative to the housing from a first longitudinal position to a second longitudinal position whereby upon movement of the first and second seals from the first longitudinal position toward the second longitudinal position, the outer base segments moves in a radial outward direction to increase the inner dimension defined by the inner seal segments.

26. The surgical access assembly according to claim 25, wherein the housing includes an internal tapered portion, the outer base segments slidably coupled to the internal tapered portion.

27. The surgical access assembly according to claim 26, wherein the outer base segments of each of the first and second seals include one of a tab or groove and the internal tapered portion of the housing includes the other of a tab or groove, the tabs received within the grooves to permit longitudinal sliding movement of the outer base segments during movement of the first and second seal elements between the first and second longitudinal positions.

28. The surgical access assembly according to claim 26, wherein the first and second seals are normally biased toward the first longitudinal position.

* * * * *